United States Patent
Coric (10) Patent No.: US 11,400,155 B2
(45) Date of Patent: Aug. 2, 2022

(54) USE OF RILUZOLE, RILUZOLE PRODRUGS OR RILUZOLE ANALOGS WITH IMMUNOTHERAPIES TO TREAT CANCERS

(71) Applicant: Biohaven Pharmaceutical Holding Company Ltd., New Haven, CT (US)

(72) Inventor: Vladimir Coric, Madison, CT (US)

(73) Assignee: Biohaven Therapeutics Ltd., New Haven, CT (US)

(*) Notice: Subject to any disclaimer, the term of this patent is extended or adjusted under 35 U.S.C. 154(b) by 0 days.

(21) Appl. No.: 16/302,284

(22) PCT Filed: May 19, 2017

(86) PCT No.: PCT/US2017/033688
§ 371 (c)(1),
(2) Date: Nov. 16, 2018

(87) PCT Pub. No.: WO2017/201501
PCT Pub. Date: Nov. 23, 2017

(65) Prior Publication Data
US 2019/0290619 A1 Sep. 26, 2019

Related U.S. Application Data

(60) Provisional application No. 62/339,433, filed on May 20, 2016.

(51) Int. Cl.
| | |
|---|---|
| A61K 39/395 | (2006.01) |
| A61K 31/428 | (2006.01) |
| C07K 16/28 | (2006.01) |
| A61K 31/426 | (2006.01) |
| A61K 45/06 | (2006.01) |
| C07D 277/82 | (2006.01) |
| A61P 35/00 | (2006.01) |
| A61K 39/00 | (2006.01) |

(52) U.S. Cl.
CPC ........ *A61K 39/3955* (2013.01); *A61K 31/426* (2013.01); *A61K 31/428* (2013.01); *A61K 39/39566* (2013.01); *A61K 45/06* (2013.01); *A61P 35/00* (2018.01); *C07D 277/82* (2013.01); *C07K 16/2818* (2013.01); *A61K 2039/505* (2013.01); *C07K 2317/24* (2013.01)

(58) Field of Classification Search
CPC .. A61K 39/3955; A61K 45/06; A61K 31/426; A61K 39/39566; A61K 31/428; A61K 31/198; A61K 2300/00; C07D 277/82; C07D 16/2818; A61P 35/00; C07K 16/2818
See application file for complete search history.

(56) References Cited

U.S. PATENT DOCUMENTS

| 2013/0210872 A1* | 8/2013 | Khan ................ A61K 41/0038 514/367 |
| 2015/0045401 A1 | 2/2015 | Smith et al. |
| 2015/0148329 A1 | 5/2015 | Reitz et al. |

FOREIGN PATENT DOCUMENTS

| WO | 2013138753 A1 | 9/2013 |
| WO | 2016-073759 A1 | 5/2016 |
| WO | 2016140878 A9 | 9/2016 |
| WO | 2016140879 A1 | 9/2016 |
| WO | 2016168716 A1 | 10/2016 |
| WO | 2017059224 A1 | 4/2017 |

OTHER PUBLICATIONS

Larkin, "Combined Nivolumab and Ipilimumab or Monotherapy in Untreated Melanoma", N Engl J Med, 2015; 373:23-34.*
Chen et al. "Anti-PD-1/PD-L1 therapy of human cancer: past, present, and future" The Journal of Clinical Investigation, 2015, 125(9), 3384-3391.
McDonnell et al. "Riluzole prodrugs for melanoma and ALS: design, synthesis, and in vitro metabolic profiling" Bioorganic and Medicinal Chemistry, 2012, 20(18), 5642-5648.
Preusser et al. "Prospects of Immune Checkpoint Modulators in the Treatment of Glioblastoma" Nature Reviews Neurology, 2015, 11(9), 1-22.
Sperling et al. "Riluzole: A Potential Therapeutic Intervention in Human Brain Tumor Stem-like Cells" Oncotarget, published on May 20, 2017 (13 pages).
Teh et al. "Metabotropic Glutamate Receptors and Cancerous Growth" WIREs Membrane Transport and Signaling, 2012, 1, 211-220.
Meldrum "Glutamate as a Neurotransmitter in the Brain: Review of Physiology and Pathology" The Journal of Nutrition, 2000, 1007S-1015S.
Chen et al. "Targeting Glutamine Induces Apoptosis: A Cancer Therapy Approach" International Journal of Molecular Sciences, 2015, 16, 22830-22855.
Yelamanchi et al. "A Pathway Map of Glutamate Metabolism" Journal of Cell Communication and Signaling, 2016, 10(1), 69-75.
Hoering et al. "End Points and Statistical Considerations in Immuno-Oncology Trials: Impact on Multiple Myeloma" Future Oncology, published online on Apr. 11, 2017 (13 pages).
Ott et al. "Combination Immunotherapy: ARoad Map" Journal for ImmunoTherapy of Cancer, 2017, 5:16 (15 pages).
Hirano et al. "Blockade of B7-H1 and PD-1 by Monoclonal Antibodies Potentiates Cancer Therapeutic Immunity" Cancer Research, published Feb. 2005 (13 pages).

(Continued)

*Primary Examiner* — Sahar Javanmard (57) ABSTRACT

Disclosed are methods of treating cancer using a combination of an immunotherapeutic agent, such as, for example, a PD-1, PD-L1 or CTLA-4 checkpoint inhibitor, and a glutamate modulating agent such as riluzole or trigriluzole. Pharmaceutical compositions including the immunotherapeutic agents and glutamate modulating agents are also disclosed.

19 Claims, 2 Drawing Sheets

(56) References Cited

OTHER PUBLICATIONS

Zeng et al. "Anti-PD-1 Blockade and Stereotactic Radiation Produce Long-Term Survival in Mice with Intracranial Gliomas" International Journal of Radiation Oncology, Biology, Physics, 2013, 86, 343-349.

Kretschmer et al. "Riluzole, a glutamate release inhibitor, and motor behavior" Archives of Pharmacology, 1998, 358, abstract only.

International Search Report dated Aug. 10, 2017 issued for the corresponding application PCT/US2017/033688 (1 page).

Written Opinion dated Aug. 10, 2017 issued for the corresponding application PCT/US2017/033688 (5 pages).

International Preliminary Report on Patentability dated Nov. 20, 2018 issued for the corresponding application PCT/US2017/033688 (11 pages).

International Search Report dated Oct. 10, 2017 issued for the corresponding application PCT/US2017/033690 (4 pages).

Written Opinion dated Oct. 10, 2017 issued for the corresponding application PCT/US2017/033690 (10 pages).

International Preliminary Report on Patentability dated Nov. 20, 2018 issued for the corresponding application PCT/US2017/033690 (11 pages).

Supplemental European Search Report dated Oct. 22, 2019 and Written Opinion issued for the corresponding European Patent Application No. 17800310.9 (5 pages).

Supplemental European Search Report dated Aug. 21, 2019 and Written Opinion issued for the corresponding European Patent Application No. 17800311.7 (7 pages).

Speyer et al. "Riluzole mediates anti-tumor properties in breast cancer cells independent of metabotropic glutamate receptor-1" Breast Cancer Research and Treatment, 2016, 157, 217-228.

Sunshine J. et al. "PD-1/PD-L1 Inhibitors" Current Opinion in Pharmacology, 2015, 23, 33-38.

\* cited by examiner

Fig. 1

USE OF RILUZOLE, RILUZOLE PRODRUGS OR RILUZOLE ANALOGS WITH IMMUNOTHERAPIES TO TREAT CANCERS

CROSS REFERENCE TO RELATED APPLICATIONS

This application claims the benefit of U.S. Provisional Application Ser. No. 62/339,433 filed May 20, 2016.

FIELD OF THE INVENTION

The present invention relates to the use of riluzole, analogs of riluzole, prodrugs of riluzole and other related riluzole compounds to enhance the therapeutic effects of immunotherapeutic agents to treat oncologic diseases or cancers.

BACKGROUND OF THE INVENTION

Riluzole (6-(trifluoromethoxy)benzothiazol-2-amine) is a pharmaceutical which has been used for treatment of amyotrophic lateral sclerosis (ALS). Recently, riluzole has been shown to have other clinical benefits. For example, orally administered riluzole dosed twice a day at a total dose of 100 mg may relieve or treat neuropsychiatric symptoms and disorders, such as mood, anxiety disorder, refractory depression, obsessive-compulsive anxiety and the like. Similarly, there is some indication that high doses of riluzole may have some anti-cancer effects but it has not yet been demonstrated to possess therapeutic anti-cancer effects on its own.

In recent years, a number of anti-cancer therapies targeting the immune system have demonstrated robust efficacy across many tumor types. Despite this novel approach to treat cancers with emerging immunotherapeutic agents, many patients do not show a complete response or remission to treatment with immunotherapies. Also, certain combination immuno-oncologic agents have significant toxicity (primarily auto-immune reactions). There is an urgent need to further augment or enhance the effect of immune-oncology therapies. Examples of therapeutic approaches to cancer with immunology targeting anti-cancer agents include: anti-PD-1, anti-PD-L1, anti-CTLA4 or other immunotherapy or checkpoint inhibitor targets. Other examples of immuno-oncology targets include: CTLA4, cytotoxic T-lymphocyte-associated antigen 4; Ig, immunoglobulin; LAG3, lymphocyte activation gene 3; mAbs, monoclonal antibodies; PD-1, programmed cell death protein 1; PDL, PD-1 ligand; TIM3, T cell membrane protein 3, CD40L, A2aR, adenosine A2a receptor; B7RP1, B7-related protein 1; BTLA, B and T lymphocyte attenuator; GALS, galectin 9; HVEM, herpesvirus entry mediator; ICOS, inducible T cell co-stimulator; IL, interleukin; KIR, killer cell immunoglobulin-like receptor; LAG3, lymphocyte activation gene 3; PD-1, programmed cell death protein 1; PDL, PD-1 ligand; TGFβ, transforming growth factor-β; TIM3, T cell membrane protein 3; and CD27. Other immune targets include: Anti-VEGF-2 monoclonal antibody (Mab), Anti-EGFr Mab, IDO1 inhibitor, Anti-B7-H3 Mab, Anti-GITR Mab, Anti-CD137 Mab, Anti-CD20 Mab, IL-15 superagonist/IL-15Rα-Fc fusion protein, Anti-CXCR4 Mab, Interleukin-21, Interleukin-21, Anti-MR Mab, Anti-CD27 Mab, Anti-CSF-1R Mab, Anti-CTLA-4 MAb+GMCSF, Anti-CD30 MAb, Anti-LAG3 Mab, Anti-CD19 Mab, Anti-OX40 Mab, Anti-CD73 Mab, OX40 agonist, or other agents including bi-specific molecules, small molecules targeting the immune system or anti-drug conjugates or vaccines.

Programed Death 1 (PD-1), an inhibitory checkpoint molecule, is expressed on T cells to limit peripheral immune responses. Ligation of PD-1 with its corresponding ligands B7-H1 (PD-L1) or B7-DC (PD-L2) has been shown to result in direct inhibition of T-cell effector activation and T cell "exhaustion." PD-L1 and PD-L2 have been shown to be up-regulated on tumor cells in a variety of human cancers, representing a potential mechanism of immune escape. Furthermore, expression of PD-1 is increased in tumor-infiltrating lymphocytes. Anti-PD-1 can block the increase in PD-1 or modify its effects.

Riluzole has multiple modes of action, including acting as a glutamate modulating agent. Glutamine, a "conditionally" essential amino acid has been demonstrated to be paramount to macromolecular synthesis and tumor cell metabolism. A variety of solid malignancies have been shown to overexpress phosphate-dependent glutaminase (GLS), which converts glutamine to glutamate further emphasizing the role of glutamine in cancer metabolism. However, glutamate is a key nitrogen "waste" bank and critical in a variety of cellular metabolic pathways. As such, reduction in glutamine/glutamate levels to immune cells may reduce proliferative and effector function, limiting an anti-tumor immune mediated response. Glutamate modulators such as riluzole may be effective as part of a combination therapy with anti-cancer agents targeting the immune system to treat disease. In particular, glutamate modulators such as riluzole are used with immunotherapeutic agents, such as certain anti-cancer agents, to treat proliferative diseases such as cancer. Analogs of riluzole may also have similar effects.

A number of other glutamate modulating agents are known. These include but are not limited to memantine, n-aceticysteine, amantadine, topiramate, pregabalin, lamotrigine, ketamine, s-ketamine, AZD8108, AZD 6765, BHV-4157, dextromethorphan, AV-101, CERC-301, GLY-13, and prodrugs or analogs thereof. These glutamate modulating agents also include but are not limited to NMDA receptor antagonists, kainite receptor antagonists, AMPA receptor antagonists, metabotropic glutamate receptors, or agents that target excitatory amino acid transporters or vesicular glutamate transport. These glutamate modulators may cause a reduction in the glutamine/glutamate levels or increase the cycling of glutamate by increasing the expression of excitatory amino acid transporters, causing a reduction in reduce proliferative and effector function.

A combination therapy employing riluzole (or related compounds) with an immunotherapy agent or other anti-cancer drug, provided simultaneously or sequentially, may have excellent cancer treating properties. In fact, there may be synergistic effects. Accordingly, the present invention relates to such a combination.

SUMMARY OF THE INVENTION

The present invention uses a combination immunotherapy having a glutamate modulating agent and an immunotherapy agent to treat disease, particularly cancer. A preferred glutamate modulating agent is riluzole and a preferred immunotherapy agent is a checkpoint inhibitor such as an anti-PD-1. It appears that the glutamate modulators make the cancer cells more susceptible to the anti-cancer agents such as immunotherapeutic agents.

The glutamate modulating agents may be given orally, sublingually, subcutaneously or in any other means of delivery. The glutamate modulating agents may be in the form of a prodrug, which releases the agent in the body, a sustained release vehicle, a delayed release vehicle, or any other delivery form. The glutamate modulating agent and the immunotherapy agent may be delivered simultaneously or sequentially. If the agents are delivered sequentially, either agent may be dosed first, and the separation of time may include finishing the dosing of one agent completely before commencing the dosage of the other or they may be intermingled in time.

The preferred glutamate modulating agents include but are not limited to: amantadine, lamotrigine, memantine, with riluzole and its prodrugs being most preferred. Prodrugs of riluzole are described in U.S. patent application Ser. No. 14/385,551, U.S. patent application Ser. No. 14/410,647, PCT Application Serial No. PCT/US2016/019773 and PCT Application Serial No. PCT/US2016/019787, the disclosures of which are all incorporated herein by reference. Sublingual formulations of riluzole that provide stability and excellent properties are described in PCT Application Serial No. PCT/US2015/061106 and PCT Application Serial No. PCT/US2015/061114, the disclosures of which are also incorporated by reference.

A sublingual formulation useful in the present invention comprises an effective amount of riluzole or pharmaceutically acceptable salts, solvates, anomers, enantiomers, hydrates or prodrugs thereof. The formulation provides sufficient solubility for riluzole to be incorporated into the sublingual formulation at relatively large doses and sublingually delivered. The formulation is preferably a modified oral disintegrating formulation of riluzole. The excipients, including mannitol and gelatin, are blended, solubilized with water and deaerated before being mixed with the active pharmaceutical ingredient (or "API"), riluzole, which has been milled separately. Particle size of the API (D50) is less than about 2 microns. The mixture is lyophilized by flash freezing and then freeze-dried. The formulation has good oral palatability.

The effective amount of glutamate modulating agent for the sublingual formulation useful in the present invention to achieve a lower therapeutic dose may be less than that of orally administered agent. Moreover, effective dose of the sublingual formulation of the glutamate modulating agent may be about 1 to 95% of that of the orally administered agent. To the extent that a sublingual formulation of the immunotherapeutic agent can be made, it may also have improved properties.

The glutamate modulating agent as part of the formulation for treating cancer or symptoms may be dosed at or below about 400 mg/day, at or below about 300 mg/day, at or below about 150 mg/day, at or below about 100 mg/day, at or below about 70 mg/day, at or below about 60 mg/day, at or below about 50 mg/day, at or below about 42.5 mg/day, at or below about 37.5 mg/day at or below about 35 mg/day, at or below about 20 mg/day, at or below about 17.5 mg/day, at or below about 15 mg/day, at or below about 10 mg/day, at or below about 5 mg/day, or at or below about 1 mg/day. In addition, the immunotherapeutic agent should be dosed at about 1-100 mg/kg; for example, 1 mg/kg, 2 mg, kg, 5 mg/kg, 7.5 mg/kg, 10 mg/kg, 20 mg/kg, 25 mg/kg, 50 mg/kg, 75 mg/kg, 100 mg/kg, or any intermediate values. A preferred immunotherapeutic agent is anti-PD-1.

Dosing may be daily, alternate days, weekly or having an even higher time separation. In certain circumstances, more often dosing can be used. In addition, the glutamate modulating agent and immunotherapeutic agent can be delivered simultaneously or sequentially.

These and other aspects and features of the invention will be apparent from the drawing and the Detailed Description.

DETAILED DESCRIPTION OF THE INVENTION

The following detailed description is provided to aid those skilled in the art in practicing the present invention. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting. All publications, patent applications, patents, figures and other references mentioned herein are expressly incorporated by reference in their entirety.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The term "riluzole", as used herein, refers to a drug having a chemical structure as follows. It is currently available in the market as RILUTEK®. The term "riluzole" also refers to all prodrugs, enantiomers, or derivatives and its pharmaceutically acceptable salts.

6-(trifluoromethoxy)benzothiazol-2-amine.

The term "sublingual administration", as used herein, refers to a route of administrating a chemical agent or a drug by placing thereof under a tongue of a subject.

The term "prodrug" as used herein, is a precursor of a drug which may be administered in an altered or less active form. The prodrug may be converted into the active drug form in physiological environments by hydrolysis or other metabolic pathways.

The term "riluzole prodrug" refers to a compound which is a derivative from riluzole with modification therein. A riluzole prodrug may also refer to a compound that is metabolized into an active form of riluzole by the body.

The term "ALS", as used herein, means Amyotrophic Lateral Sclerosis.

The term "immunotherapeutic anti-cancer agent" includes any agent that targets the immune system to result in an anti-cancer therapeutic effects. Such targets and agents include but are not limited to: anti-PD-1, anti-PD-L1, anti-CTLA4 or other immunotherapy or checkpoint inhibitor targets. Other examples of immuno-oncology targets include: CTLA4, cytotoxic T-lymphocyte-associated antigen 4; Ig, immunoglobulin; LAG3, lymphocyte activation gene 3; mAbs, monoclonal antibodies; PD-1, programmed cell death protein 1; PDL, PD-1 ligand; TIM3, T cell membrane protein 3, CD40L, A2aR, adenosine A2a receptor; B7RP1, B7-related protein 1; BTLA, B and T lymphocyte attenuator; GALS, galectin 9; HVEM, herpesvirus entry mediator; ICOS, inducible T cell co-stimulator; IL, interleukin; KIR, killer cell immunoglobulin-like receptor; LAG3, lymphocyte activation gene 3; PD-1, programmed cell death protein 1; PDL, PD-1 ligand; TGFβ, transforming growth factor-β; TIM3, T cell membrane protein 3; and CD27. Other immune targets include: Anti-VEGF-2 monoclonal antibody (Mab), Anti-EGFr Mab, IDO1 inhibitor, Anti-B7-H3 Mab, Anti-GITR Mab, Anti-CD137 Mab, Anti-CD20 Mab, IL-15 superagonist/IL-15Rα-Fc fusion protein, Anti-CXCR4 Mab, Interleukin-21, Interleukin-21, Anti-MR Mab, Anti-CD27 Mab, Anti-CSF-1R Mab, Anti-CTLA-4 MAb+GMCSF, Anti-CD30 MAb, Anti-LAG3 Mab, Anti-CD19 Mab, Anti-OX40 Mab, Anti-CD73 Mab, OX40 agonist, or other agents including bi-specific molecules, small molecules targeting the immune system or anti-drug conjugates or vaccines, or nivolumab (Opdivo), pembrolizumab (Keytruda), pidilizumab, ipilimumab (Yervoy), PDR001, MEDI0680, atezolizumab, durvalumab or combinations thereof.

The term "cancer" includes, but is not limited to, the following proliferative diseases: Acute Lymphoblastic Leukemia (ALL), Acute Myeloid Leukemia (AML), Adrenocortical Carcinomas, Childhood cancers, AIDS-Related Cancers, Kaposi Sarcoma, AIDS-Related Lymphoma, Primary CNS Lymphoma, Anal Cancer, Astrocytomas, Atypical Teratoid/Rhabdoid Tumor, Basal Cell Carcinoma, Skin Cancer (Nonmelanoma), Bile Duct Cancer, Bladder Cancer, Bone Cancer, Ewing Sarcoma Family of Tumors, Osteosarcoma and Malignant Fibrous Histiocytoma, Brain Stem Glioma, Atypical Teratoid/Rhabdoid Tumor, Embryonal Tumors, Germ Cell Tumors, Craniopharyngioma, Ependymoma, Breast Cancer, Bronchial Tumors, Burkitt Lymphoma, Non-Hodgkin Lymphoma, Carcinoid Tumor, Gastrointestinal Carcinoma, Cardiac (Heart) Tumors, Primary Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Mycosis Fungoides and Sézary Syndrome, Ductal Carcinoma In Situ (DCIS), Embryonal Tumors, Endometrial Cancer, Ependymoma, Esophageal Cancer, Esthesioneuroblastoma, Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Germ Cell Tumor, Ovarian, Testicular, Gestational Trophoblastic Disease, Glioma, Hairy Cell Leukemia, Head and Neck Cancer, Hepatocellular (Liver) Cancer, Histiocytosis, Langerhans Cell, Hodgkin Lymphoma, Hypopharyngeal Cancer, Islet Cell Tumors, Pancreatic Neuroendocrine Tumors, Kaposi Sarcoma, Kidney, Renal Cell, Langerhans Cell Histiocytosis, Laryngeal Cancer, Leukemia, Acute Lymphoblastic (ALL), Acute Myeloid (AML), Chronic Lymphocytic (CLL), Chronic Myelogenous (CML), Hairy Cell, Lip and Oral Cavity Cancer, Liver Cancer (Primary), Lung Cancer, Non-Small Cell, Small Cell, Lymphoma, Hodgkin, Non-Hodgkin, Macroglobulinemia, Waldenström, Male Breast Cancer, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML) Myeloma, Multiple, Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Ovarian Cancer, Low Malignant Potential Tumor, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Rhabdomyosarcoma, Uterine, Small Intestine Cancer, Soft Tissue Sarcoma, Squamous Cell Carcinoma, Squamous Neck Cancer with Occult Primary, Metastatic, Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Unknown Primary, Ureter and Renal Pelvis, Transitional Cell Cancer, Urethral Cancer, Uterine Cancer, Endometrial, Uterine Sarcoma, Vaginal Cancer, Vulvar Cancer, Waldenström Macroglobulinemia, and Wilms Tumor.

The term "treatment" as used herein includes any treatment of a condition or disease in a subject, or particularly a human, and may include: (i) preventing the disease or condition from occurring in the subject which may be predisposed to the disease but has not yet been diagnosed as having it; (ii) inhibiting the disease or condition, i.e., arresting its development; relieving the disease or condition, i.e., causing regression of the condition; or (iii) ameliorating or relieving the conditions caused by the disease, i.e., symptoms of the disease. "Treatment," as used herein, could be used in combination with other standard therapies or alone.

The term "effective" is used to describe an amount of a compound, composition or component which, when used within the context of its intended use, effects an intended result.

The term "effective amount" refers to that amount which is sufficient to effect treatment, as defined herein, when administered to a subject in need of such treatment. The effective amount will vary depending on the subject and disease state being treated, the severity of the affliction and the manner of administration, and may be determined routinely by one of ordinary skill in the art.

The term "pharmaceutically acceptable salt" is used throughout the specification to describe, where applicable, a salt form of one or more of the compounds or prodrugs described herein which are presented to increase the solubility of the compound in the gastric or gastroenteric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present invention. In a preferred embodiment, the description provides pharmaceutically acceptable salts of the modified peptides as described herein, which retain the biological effectiveness and properties of the parent compounds and which are not biologically or otherwise harmful as the dosage administered. The compounds of this invention are capable of forming both acid and base salts by virtue of the presence of amino and carboxy groups respectively.

The term "Cmax", as used herein, refers to a maximum concentration of a drug in blood, serum, a specified compartment or test area of a subject between administration of a first dose and administration of a second dose. The term Cmax could also refer to dose normalized ratios if specified.

The term "Tmax", as used herein, refers to a time or period after administration of a drug when the maximum concentration (Cmax) is reached in blood, serum, a specified compartment or test area of a subject.

The term "AUC" (area under the curve), as used herein, refers to a total amount of drug absorbed or exposed to a subject. Generally, AUC may be obtained from mathematical method in a plot of drug concentration in the subject over time until the concentration is negligible. The term "AUC" (area under the curve) could also refer to partial AUC at specified time intervals (as may be the case with sublingual absorption which would increase AUC at earlier time intervals).

The invention relates to a combination therapy utilizing an immunotherapeutic agent and a glutamate modulating agent. The combination of these two drugs may be administered in a single dose as combined product, administered simultaneously using the same or distinct formats, or administered sequentially using the same or different forms of delivery. For example, if the immunotherapeutic agent and the glutamate modulating agent can both be made into a tablet or part of a sublingual form, they can be administered together. Similarly, if the immunotherapeutic agent can only be administered by injection (bolus or intravenous), and the glutamate modulating agent can be administered in the same format, this could also be used for simultaneous or sequential administration. However, if the immunotherapeutic agent can only be delivered by injection (for example, if it is an antibody), and the glutamate modulating agent can be delivered as a tablet or sublingually, delivery of the two agents can take place by differing formats.

Some of the glutamate modulating agents can be administered sublingually. PCT Application No. PCT/US2015/061106 and PCT Application No. PCT/US2015/061114 describe a sublingual formulation of riluzole, a preferred glutamate modulating agent. The sublingual formulation may be administered in an effective amount to a subject in need thereof. The subject may be an animal or human.

For use with the current invention, the glutamate modulating agent or its pharmaceutically acceptable salts thereof may be formulated in a pharmaceutical composition suitable for sublingual administration. In some circumstances, the immunotherapeutic agent may also be formulated as a sublingual, although injection is more standard.

Glutamate modulating agents such as riluzole and the pharmaceutically acceptable salts thereof can be formulated using pharmaceutically acceptable carriers well known in the art into dosages suitable for sublingual or buccal administration. Such carriers enable the glutamate modulating agent for sublingual administration to be formulated in dosage forms such as tablets, powders, pills, capsules, liquids, gels, syrups, slurries, suspensions, and the like, for sublingual absorption by a subject to be treated. These carriers may be, but not limited to, selected from sugars, starches, cellulose and its derivatives, malt, gelatin, talc, calcium sulphate, vegetable oils, synthetic oils, polyols, alginic acid, phosphate buffered solutions, emulsifiers, isotonic saline, pyrogen-free water and combinations thereof. In particular, any form of substance may be accepted to sublingual administration if it dissolves easily in saliva.

The sublingually administered chemical agent or the drug can diffuse into capillaries through mucous membrane under the tongue, and then enter venous circulation of the subject. As such, sublingual administration may have advantages over oral administration as allowing for direct or faster entry to venous circulation, without risks of degradation in gastrointestinal tract, alteration by drug metabolism in liver and the like. Various drugs in the market are designed for sublingual administration. Riluzole is generally used to treat amyotrophic lateral sclerosis (ALS). However, other uses have been found, and in particular, riluzole or prodrugs of riluzole or pharmaceutically acceptable salts thereof is subjected to a sublingual administration for the treatment of other disorders, including cancer.

The pharmaceutical composition may include an approved pharmaceutical ingredient, i.e., riluzole, in an effective amount to achieve their intended purpose. For example, the dose of the glutamate modulating agent administered sublingually to the subject should be sufficient to provide a beneficial response in the subject over time such as reduction in symptoms in conjunction with the immunotherapeutic agent. The combination may have synergistic effects.

The quantity of the glutamate modulating agent and the quantity of the immunotherapeutic agent to be administered may depend on the subject to be treated inclusive of the age, sex, weight and general health condition thereof. In this regard, precise amounts of the agent(s) for administration will depend on the judgment of the practitioner. In determining the effective amount of the glutamate modulating agent and immunotherapeutic agent to be administered in the treatment or reducing of the conditions associated with the symptoms and disorders, the physician may evaluate clinical factors including symptoms severity or progression of the disorder. In some conditions, a rapid absorption of the glutamate modulating agent or immunotherapeutic agent may be desirable. In any event, those of skill in the art may readily determine suitable dosages of the chemical agents of the invention.

The pharmaceutical composition also includes other pharmaceutically acceptable carriers and/or excipients such as binders, lubricants, diluents, coatings, disintegrants, barrier layer components, glidants, coloring agents, solubility enhancers, gelling agents, fillers, proteins, co-factors, emulsifiers, solubilizing agents, suspending agents and mixtures thereof. A skilled artisan in the art would know what other pharmaceutically acceptable carriers and/or excipients could be included in the formulations according to the invention. The choice of excipients would depend on the characteristics of the compositions and on the nature of other pharmacologically active compounds in the formulation. Appropriate excipients are known to those skilled in the art (see Handbook of Pharmaceutical Excipients, fifth edition, 2005 edited by Rowe et al., McGraw Hill) and have been utilized to yield a novel sublingual formulation with unexpected properties.

In addition, the pharmaceutical composition for sublingual use can be obtained by combining an approved pharmaceutical ingredient, i.e., riluzole, with further excipients, with optionally processing to obtain dosage forms such as tablets, powders, pills, capsules, liquids, gels, syrups, slurries, suspensions, and the like, for sublingual absorption by a subject to be treated. Suitable excipients may be, but not limited to, fillers such as sugars, including lactose, sucrose, mannitol, or sorbitol; cellulose preparations such as maize starch, wheat starch, rice starch, potato starch, gelatin, gum tragacanth, methyl cellulose, hydroxypropyl methyl-cellulose, sodium carboxymethylcellulose, and/or polyvinyl-pyrrolidone (PVP). If desired, disintegrating agents may be combined as well, and exemplary disintegrating agents may be, but not limited to, cross-linked polyvinyl pyrrolidone, agar, or alginic acid or a salt thereof such as sodium alginate. The compositions may be prepared by any of the methods of pharmacy but all methods include the step of bringing into association one or more chemical agents as described above with the carrier which constitutes one or more necessary ingredients. In general, the pharmaceutical compositions of the present invention may be manufactured in conventional methods known in the art, for example, by means of conventional mixing, dissolving, granulating, dragee-making, levigating, emulsifying, encapsulating, entrapping, lyophilizing processes and the like.

The sublingual formulation useful in the combination product of the invention may be prepared in a form of an orally dissolving or disintegrating tablet (ODT). The ODT as used herein may be prepared by mixing the glutamate modulating agent and/or the immunotherapeutic agent with water-soluble diluents and compressed in a tablet. A suspension comprising the active product may be prepared with appropriate excipients and the suspension may be dispensed into blister packs and freeze-dried. An exemplary freeze-dried preparation platform that could be used for the ODT is the ZYDIS® (Catalent, Somerset, N.J., USA) formulation. In particular, the excipients, including water, are blended and the glutamate modulating agent is separately milled to size and mixed with the excipients. The suspension then undergoes lyophilisation by flash freezing and freeze drying. Other methods of preparing ODTs may be used without limitation, and detailed description of general methods thereof have been disclosed, for example, in U.S. Pat. Nos. 5,631,023; 5,837,287; 6,149,938; 6,212,791; 6,284,270; 6,316,029; 6,465,010; 6,471,992; 6,471,992; 6,509,040; 6,814,978; 6,908,626; 6,908,626; 6,982,251; 7,282,217; 7,425,341; 7,939,105; 7,993,674; 8,048,449; 8,127,516; 8,158,152; 8,221,480; 8,256,233; and 8,313,768, each of which is incorporated herein by reference in its entirety.

The sublingual formulation useful in the invention may comprise the glutamate modulating agent or an effective amount of a glutamate modulating agent prodrug. Similarly, in certain circumstances, the immunotherapeutic agent may be made into a prodrug. The prodrug may be similar or less active form of the active. The prodrug may have improved physiochemical, physiological pharmacokinetic or therapeutical characteristics when administered sublingually. The prodrug may reduce side effects when orally or sublingually administered.

The clinical or therapeutic effect of the compound, or a subportion of the final product, sublingually formulated may have an improved pharmacokinetic profile for the pharmaceutical agent as measured by standard testing parameters. When the glutamate modulating agent or the total composition is administered sublingually, the Tmax, Cmax and AUC of the drug may be improved compared to the same dose of the orally administered version of the same compound. For example, the sublingual formulation of the glutamate modulating agent may have a greater Cmax than the orally administered glutamate modulating agent to provide a therapeutically beneficial effect. The sublingual formulation of the glutamate modulating agent may have an earlier or lesser Tmax than the orally administered glutamate modulating agent to provide a therapeutically beneficial effect and in some instances, a more rapid therapeutic effect. Alternatively, the sublingual formulation of the glutamate modulating agent may have a greater AUC per milligram of the agent than the orally administered glutamate modulating agent. In addition, as the glutamate modulating agent may make the immunotherapeutic agent more effective, lesser amounts of the immunotherapeutic agent may be needed to achieve the same results, with a lessening of the inherent side effects.

The invention provides a method of treating a disease such as cancer. The method comprises administering sublingually an effective amount of glutamate modulating agent or pharmaceutically acceptable salts thereof and an anticancer agent, preferably an immunotherapeutic agent, or pharmaceutically acceptable salts thereof to a subject in need thereof.

Identifying the subject in need of such treatment can be in the judgment of the subject or a health care professional and can be subjective (e.g., opinion) or objective (e.g., measurable by a test or diagnostic method). The identified subject may be an animal or human in need thereof, particularly a human. Such treatment will be suitably administered to subjects, particularly humans, suffering from the disease.

The effective amount of the treatment will vary depending on the subject and disease state being treated, the severity of the affliction and the manner of administration, and may be determined routinely by one of ordinary skill in the art.

The therapeutic effect of the combination product, particularly as it applies to treating symptoms, may be evident to occur within about a few minutes to about an hour after administration thereof. In particular, the therapeutic effect may begin within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 16 minutes, within about 17 minutes, within about 18 minutes, within about 20 minutes, within about 60 minutes, or within about 90 minutes after administration. However, long term cure or amelioration of the disease may not occur for weeks or months after administration.

The effects on the symptoms may be maintained for about 1 hour, for about 2 hours, for about 3 hours, for about 4 hours, for about 5 hours, for about 6 hours m for about 7 hours, for about 8 hours, for about 9 hours, for about 10 hours, for about 12 hours for about 14 hours for about 16 hours for about 18 hours, for about 20 hours for about 22 hours for about 24 hours for about 2 days, or for about 3 days or more after administration thereof. Hopefully, once the long term effects on the disease state is achieved, the disease, and the symptoms, will be eliminated permanently.

The effective amount or dose of glutamate modulating agent for sublingual administration may be less than that of orally administered agent. In particular, the effective dose in sublingual administration of the glutamate modulating agent, such as riluzole, may be of about 1-95% of the dose of the orally administered agent itself. In addition, similar reduction in the amount of the immunotherapeutic agent may be achieved by administration of the glutamate modulating agent itself, by any mode of administration.

Optional dosage frequencies include once a day, twice a day, three times a day, four times a day, once every other day, once a week, twice a week, three times a week, four times a week, once every two weeks, once or twice monthly, and the like.

Glutamate modulating agents can be used as is or may be in the form of prodrugs. Prodrugs of riluzole are described in U.S. patent application Ser. No. 14/385,551, U.S. patent application Ser. No. 14/410,647, PCT Application Serial No. PCT/US2016/019773 and PCT Application Serial No. PCT/US2016/019787. The preferred riluzole prodrugs have the structure:

including enantiomers, diastereomers, hydrates, solvates, pharmaceutically acceptable salts, and complexes thereof, wherein:

$R_{23}$ is selected from the group consisting H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$.

A preferred prodrug of riluzole has the following formula:

Those skilled in the art will recognize that similar or variant prodrugs can be made from other glutamate modulating agents. Such agents are useful as part of the combination of the present invention.

Example

The following example illustrates the invention and is not intended to limit the scope of the invention.

In this Example, the effects of the combination of a glutamate modulator, BHV-4157, in combination with an immunotherapeutic agent, anti-PD-1, were compared to either alone in a glioma model substantially as described in Zeng, J., et al., Int J Radiat Oncol Biol Phys., 2013 Jun. 1; 86(2):343-349, portions of which are reproduced below.

Cells

GL261-Luc cells are grown in Dulbecco's Modified Eagle Medium (DMEM)+10% fetal bovineserum+1% penicillinstreptomycin at 37° C. in a humidified incubator maintained at 5% CO and 5% $O_2$ (Gibco).

Tumor Model

Female C57BL/6J mice (Harlan), 4 to 6 weeks old or 6 to 8 weeks old, are used for orthotopic glioma experiments as described in Sonabend A M, Velicu S, Ulasov I V, et al. A safety and efficacy study of local delivery of interleukin12 transgene by PPC polymer in a model of experimental glioma. Anticancer Drugs. 2008; 19:133-142. To establish syngeneic gliomas, 130,000 GL261-Luc cells are stereotactically injected in a 1 μL volume into the left striatum over 1 minute into the following coordinates: 1 mm anterior, 1 mm lateral from bregma, and 3 mm deep from the cortical surface. Tumor burden is monitored by luciferase imaging on days 7, 21 and 35 after implantation, and the mice are randomly allocated into treatment arms based on tumor radiance, so that the average tumor radiance in each group is roughly equivalent. The animals are euthanized when they show predetermined signs of neurologic deficits (failure to ambulate, weight loss>20% body mass, lethargy, hunched posture). The tumor take rate is 100%. Each arm has 6 to 10 mice in survival experiments. All experiments are repeated at least in triplicate.

Anti-PD-1 Antibodies

Hamster antimurine PD-1 monoclonal antibody producing hybridoma G4 are used to produce antibodies as described in Hirano F, Kaneko K, Tamura H, et al. Blockade of B7-H1 and PD-1 by monoclonal antibodies potentiates cancer therapeutic immunity. Cancer Res. 2005; 65:1089-1096.

Specific Protocol

Figure 2:
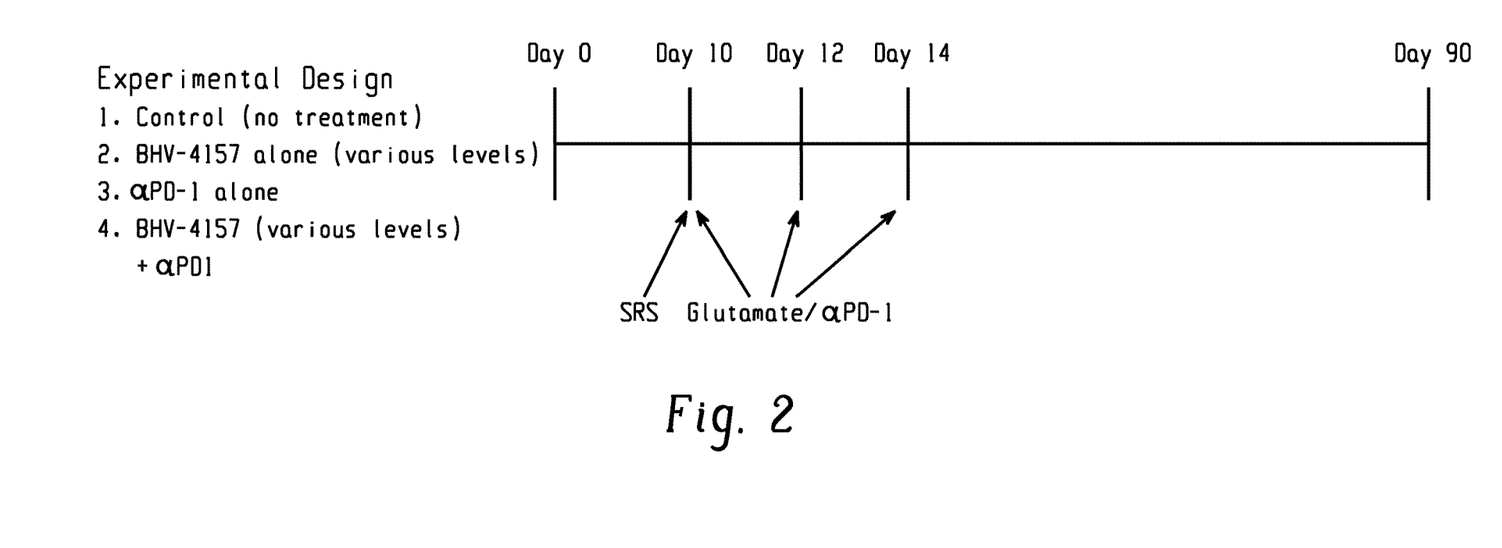
FIG. 2 of the Drawings illustrates the specific protocol of the study described in Example 1.

Female C57BL/6J mice, 4 to 6 weeks old, were implanted intracranially in the left striatum with 130,000 GL261 cells each. The mice were housed and maintained according to the Institutional Animal Care and Use Committee protocol in the Johns Hopkins University Animal Facility. The mice were imaged by bioluminescent IVIS® imaging (Perkin Elmer) at day 7, 21, and 35 to assess tumor burden and randomly assigned to groups, 10 mice per arm, as follows:
1. Control
2. anti-PD-1
3. Trigriluzole 15 mg/kg
4. Trigriluzole 30 mg/kg
5. Trigriluzole 45 mg/kg
6. anti-PD-1+Trigriluzole 15 mg/kg,
7. anti-PD-1+Trigriluzole 30 mg/kg
8. anti-PD-1+Trigriluzole 45 mg/kg The protocol is shown in the following illustration:
The protocol is shown in FIG. 2.

Day 0 represents the date of intracranial implantation. Control arm 1 received no treatment. Control arm 2 received αPD-1 alone at a dose of 200 μg/animal via intraperitoneal injection on days 10, 12, 14. Control arms 3, 4 and 5 received BHV-4157 alone at doses of 15, 30 and 45 mg/kg (respectively) via intraperitoneal injection daily beginning on day 10. Control arms 6, 7 and 8 received BHV-4157 at doses of 15, 30 and 45 mg/kg (respectively) via intraperitoneal injection daily beginning on day 10 and αPD-1 at a dose of 200 μg/animal via intraperitoneal injection on days 10, 12, 14.

The treatment was terminated when mice showed no tumor burden via IVIS imaging. Animals were euthanized according to humane endpoints including central nervous system disturbances, hunched posture, lethargy, weight loss, and inability to ambulate.

Figure 1:
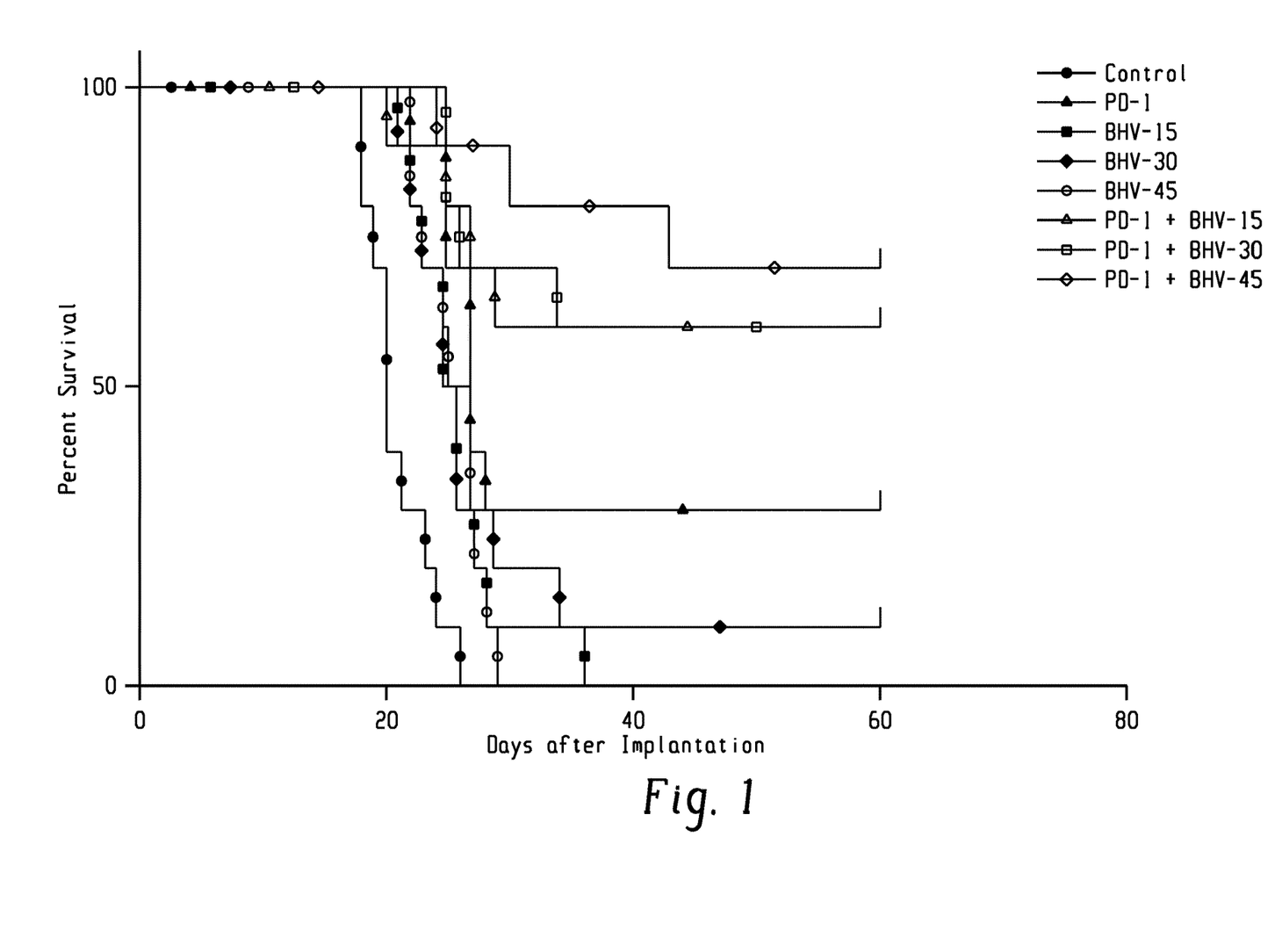
FIG. 1 of the Drawings illustrates the results of the test described in Example 1, testing three levels of a riluzole prodrug (BHV-4157), anti-PD-1, various combinations of anti-PD-1 and BHV-4157 and a control, to see if the combination modified survival in a glioblastoma animal model.

The purpose of the experiment was to see if the combination therapy was provided a benefit over either therapy alone. The results are shown in FIG. 1. As is evident from FIG. 1, the combination therapy is substantially better than any of the individual therapies and that the effects are not merely additive but appear synergistic.

Thus, it appears that the glutamate modulators effect on glutamate/glutamine metabolism weakens the tumor cells and makes the anti-PD-1 antibody more effective. Quite surprisingly, in accordance with the present invention, the percentage survival of mice at about 30, 40 and 60 days after implantation was about 2 times, or greater, the percent survival for the mice treated with the glutamate modulator in combination with the immunotherapeutic anti-cancer agent as compared to the immunotherapeutic anti-cancer agent alone. Table 1 below shows data from Example 1.

Accordingly, at day 28, the Mouse Survival Ratio ($MSR_{28}$) was about 2.0 to 2.6 (i.e., 60/30 and 80/30). At day 60, the mice in Arm 1 (Control) had 0% survival, the mice in Arm 2 (PD-1) had 30% survival and the mice in Arms 6, 7 and 8 had 60 to 70% survival. Accordingly, at day 60, the Mouse Survival Ratio ($MSR_{60}$) was about 2.0 to 2.3 (i.e., 60/30 and 70/30). Preferably, in accordance with the present invention, the Mouse Survival Ratio is at least 1.4, more preferably at least 1.6 when measured at 26 days after tumor implantation ($MSR_{26}$). Preferably, in accordance with the present invention, the Mouse Survival Ratio is at least 2.0, more preferably at least 2.6 when measured at 28 days after tumor implantation ($MSR_{28}$). Preferably, in accordance with the present invention, the Mouse Survival Ratio is at least 2.0, more preferably at least 2.3 when measured at 60 days after tumor implantation ($MSR_{60}$). Preferably, in accordance with the present invention, the Mouse Survival Ratio measured at a time when the untreated mice reach 0% survival, or thereafter until a time of 60 days after tumor implantation, is at least 1.4, at least 1.6, at least 2.0, at least 2.3 or at least 2.6.

Typically, combination therapy, i.e., an immunotherapeutic anti-cancer agent and a glutamate modulating agent, in accordance with the present invention will provide a Mouse

TABLE 1

PERCENT SURVIVAL OF MICE AFTER TUMOR IMPLANTATION

| Days after Tumor Implantation | Arm1 Control | Arm 2 PD-1 | Arm 3 BHV-4157 15 mg/kg | Arm 4 BHV-4157 30 mg/kg | Arm 5 BHV-4157 45 mg/kg | Arm 6 PD-1 + BHV-4157 15 mg/kg | Arm 7 PD-1 + BHV-4157 30 mg/kg | Arm 8 PD-1 + BHV-4157 45 mg/kg |
|---|---|---|---|---|---|---|---|---|
| 0 | 100 | 100 | 100 | 100 | 100 | 100 | 100 | 100 |
| 18 | 80 | | | | | | | |
| 19 | 70 | | | | | | | |
| 20 | 40 | | | | | 90 | | |
| 21 | 30 | | 90 | 90 | 90 | | | |
| 22 | | 90 | 80 | | 80 | | | |
| 23 | 20 | 80 | 70 | 70 | 70 | | | |
| 24 | 10 | | 50 | 50 | 60 | | | 90 |
| 25 | | 70 | | | 50 | 80 | 80 | |
| 26 | 0 | 50 | 30 | 30 | | | 70 | |
| 27 | | 40 | 20 | | 20 | 70 | | |
| 28 | | 30 | 10 | | 10 | | | |
| 29 | | | | 20 | 0 | 60 | | |
| 30 | | | | | | | | 80 |
| 34 | | | | 10 | | | 60 | |
| 36 | | | | 0 | | | | |
| 43 | | | | | | | | 70 |
| 60 | | 30 | | 10 | | 60 | 60 | 70 |

The term "Mouse Survival Ratio", also referred to as "$MSR_x$," refers to a value calculated by dividing: (i) the percentage survival of mice treated with an immunotherapeutic anti-cancer agent plus a glutamate modulating agent, by (ii) the percentage survival of mice treated with an immunotherapeutic anti-cancer agent alone, in accordance with the procedure set forth in Example 1 hereof at a time period of "x" number of days after implantation of the tumor into the mice. Thus, $MSR_{60}$ refers to the Mouse Survival Ratio at a time of 60 days after tumor implantation.

From Table 1, it can be seen that by day 26, the mice in Arm 1 (Control) had 0% survival, the mice in Arm 2 (PD-1) had 50% survival and the mice in Arms 6, 7 and 8 had at least 70 to 80% survival. Accordingly, at day 26, the Mouse Survival Ratio ($MSR_{26}$) was about 1.4 to 1.6 (i.e., 70/50 and 80/50). At day 28, the mice in Arm 1 (Control) had 0% survival, the mice in Arm 2 (PD-1) had 30% survival and the mice in Arms 6, 7 and 8 had at least 60 to 80% survival.

Survival Ratio of at least 2.0, more typically at least 2.3 (measured at day 60, $MSR_{60}$). The results are shown in FIG. 1. As is evident from FIG. 1, the combination therapy is substantially better than any of the individual therapies and that the effects are not merely additive but appear synergistic. Thus, it appears that the glutamate modulators effect on glutamate/glutamine metabolism weakens the tumor cells and makes the anti-PD-1 more effective.

A variety of solid malignancies have been shown to overexpress phosphate-dependent glutaminase (GLS), which converts glutamine to glutamate further emphasizing the role of glutamine in cancer metabolism. However, glutamate is a key nitrogen "waste" bank and critical in a variety of cellular metabolic pathways. As such, reduction in glutamine/glutamate levels to immune cells may reduce proliferative and effector function, limiting an anti-tumor immune mediated response. While this effect is clear for GLS producing tumor cells, glutamate receptors are found on a number of other tumor cells and it is believed that this combination therapy could be effective for those cells as well.

The entire contents of all patents, published patent applications and other references cited herein are hereby expressly incorporated herein in their entireties by reference.

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A method of treating cancer by administering a combination therapy to a patient in need thereof comprising of an effective amount of a riluzole prodrug having formula:

and an inhibitor of a checkpoint receptor selected from PD-1 and PD-L1, wherein the cancer is bladder cancer, breast cancer, colorectal cancer, gastrointestinal cancer, glioblastoma, lymphoma, melanoma, non-small cell lung cancer, ovarian cancer, prostate cancer, renal cell carcinoma, solid malignancy, and squamous cell carcinoma of head and neck.

2. The method of claim 1, wherein riluzole prodrug and the checkpoint inhibitor are administered either concurrently or sequentially in time.

3. The method of claim 1, wherein said checkpoint inhibitor is selected from the group consisting of nivolumab, pembrolizumab, pidilizumab, PDR001, MEDI0680, atezolizumab, durvalumab and combinations thereof.

4. The method of claim 1, wherein said combination of riluzole and checkpoint inhibitor is administered in combination or sequentially with other anti-cancer standard of care treatments.

5. The method of claim 1, wherein the riluzole and the checkpoint inhibitor are capable of providing a Mouse Survival Ratio of at least 2.0 at day 60 ($MSR_{60}$).

6. The method of claim 3, wherein the riluzole and the checkpoint inhibitor are capable of providing a Mouse Survival Ratio of at least 2.0 at day 60 ($MSR_{60}$).

7. The method of claim 1, wherein the cancer is bladder cancer.

8. The method of claim 1, wherein the cancer is breast cancer.

9. The method of claim 1, wherein the cancer is colorectal cancer.

10. The method of claim 1, wherein the cancer is gastrointestinal cancer.

11. The method of claim 1, wherein the cancer is glioblastoma.

12. The method of claim 1, wherein the cancer is lymphoma.

13. The method of claim 1, wherein the cancer is melanoma.

14. The method of claim 1, wherein the cancer is non-small cell lung cancer.

15. The method of claim 1, wherein the cancer is ovarian cancer.

16. The method of claim 1, wherein the cancer is prostate cancer.

17. The method of claim 1, wherein the cancer is renal cell carcinoma.

18. The method of claim 1, wherein the cancer is solid malignancy.

19. The method of claim 1, wherein the cancer is squamous cell carcinoma of head and neck.

* * * * *